(12) United States Patent
Slanda et al.

(10) Patent No.: US 6,699,233 B2
(45) Date of Patent: Mar. 2, 2004

(54) LOCKING CATHETER

(75) Inventors: Jozef Slanda, Milford, MA (US); Clifford M. Liu, Randolph, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 484 days.

(21) Appl. No.: 09/829,731

(22) Filed: Apr. 10, 2001

(65) Prior Publication Data

US 2001/0049490 A1 Dec. 6, 2001

Related U.S. Application Data

(60) Provisional application No. 60/195,931, filed on Apr. 10, 2000.

(51) Int. Cl.[7] ................................................. F15B 7/00
(52) U.S. Cl. ....................... 604/533; 604/523; 604/534; 604/535; 604/540
(58) Field of Search ............................... 604/264, 523, 604/528, 533, 534, 535, 540, 905; 285/305

(56) References Cited

U.S. PATENT DOCUMENTS

| | | |
|---|---|---|
| 3,108,595 A | 10/1963 | Overment |
| 3,946,741 A | 3/1976 | Adair |
| 3,983,203 A | 9/1976 | Corbett |
| 4,405,163 A | 9/1983 | Voges et al. |
| 4,643,720 A | 2/1987 | Lanciano |
| 4,699,611 A | 10/1987 | Bowden |
| 4,740,195 A | 4/1988 | Lanciano |
| 5,041,085 A | 8/1991 | Osborne et al. |
| 5,047,021 A | 9/1991 | Utterberg |
| 5,352,198 A | 10/1994 | Goldenberg et al. |
| 5,399,165 A | 3/1995 | Paul, Jr. |
| 5,419,764 A | 5/1995 | Roll |
| 5,522,400 A | 6/1996 | Williams |
| 5,542,716 A * | 8/1996 | Szabo et al. ................ 285/305 |
| 5,620,427 A | 4/1997 | Werschmidt et al. |
| 5,741,301 A | 4/1998 | Pagedas |
| 5,746,722 A | 5/1998 | Pohndorf et al. |
| 5,803,509 A * | 9/1998 | Adams ........................ 285/114 |
| 5,871,475 A * | 2/1999 | Frassica ....................... 604/264 |
| 5,928,208 A | 7/1999 | Chu et al. |
| 5,941,849 A | 8/1999 | Amos, Jr. et al. |
| 5,971,950 A | 10/1999 | Lopez et al. |
| 5,989,241 A | 11/1999 | Plishka et al. |
| 6,027,143 A * | 2/2000 | Berg et al. ..................... 285/93 |
| 6,042,577 A | 3/2000 | Chu et al. |
| 6,159,177 A | 12/2000 | Amos, Jr. et al. |
| 6,595,556 B1 * | 7/2003 | Zenko et al. ................ 285/305 |

FOREIGN PATENT DOCUMENTS

JP          08252320          11/1995

* cited by examiner

*Primary Examiner*—Weilun Lo
*Assistant Examiner*—Michael Bogart
(74) *Attorney, Agent, or Firm*—Testa, Hurwitz & Thibeault, LLP

(57) ABSTRACT

An apparatus and method for locking a catheter within a patient enables the catheter to be easily and securely locked and prevents the catheter from being inadvertently unlocked. The locking catheter includes an elongated body member including a proximal portion and a distal portion, a first proximal member, an elongated flexible member, and a second proximal member releasably couplable to the first proximal member to allow selective locking and unlocking of the elongated flexible member therebetween. The second proximal member includes a channel. The elongated flexible member extends from the distal portion of the elongated body member, through the first proximal member, and through the channel of the second proximal member. The elongated flexible member is slidable through the channel thereby allowing the distal portion of the elongated body member to be drawn toward the proximal portion of the elongated body member to form a loop in the distal portion of the elongated body member.

17 Claims, 19 Drawing Sheets

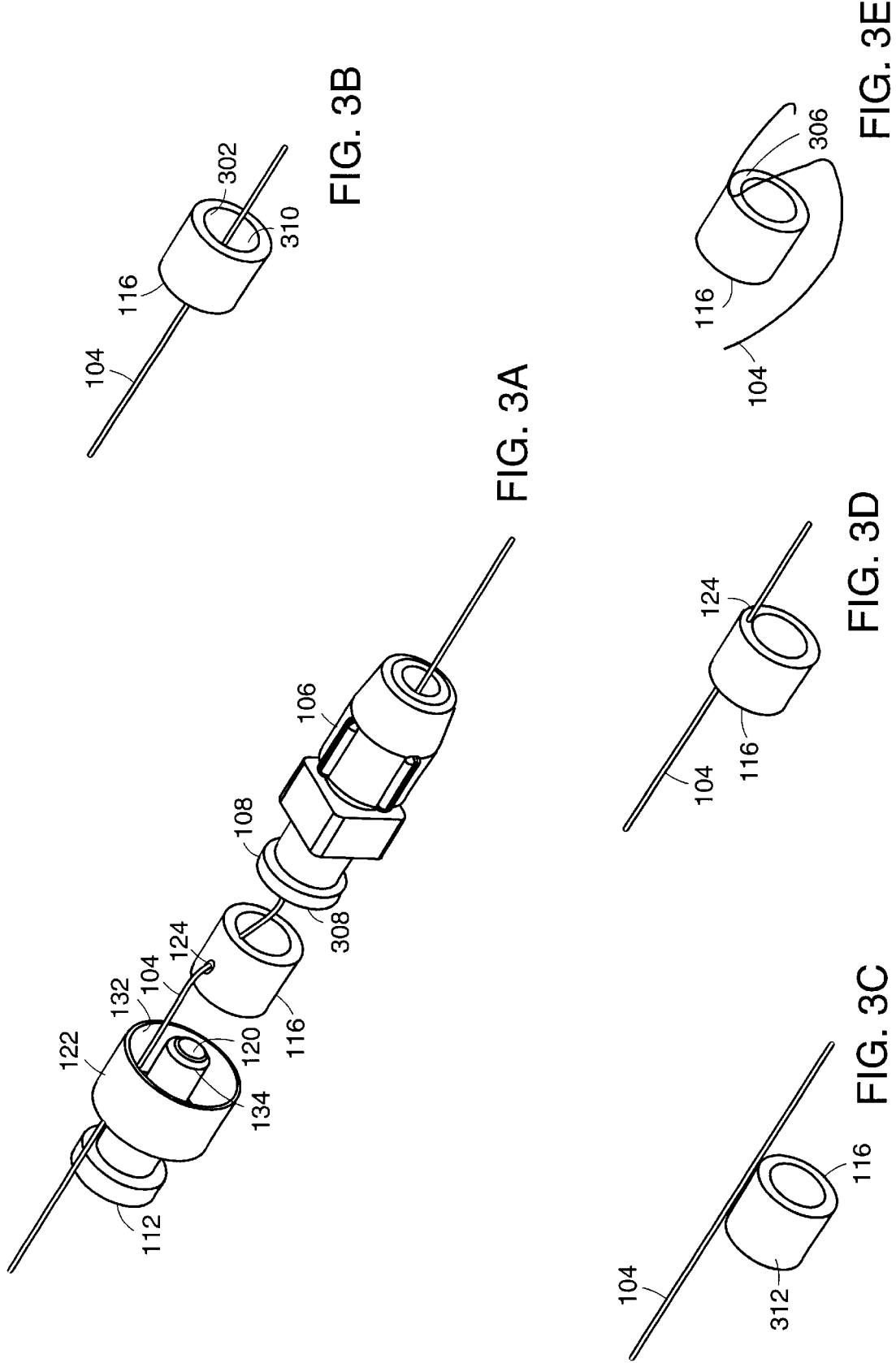

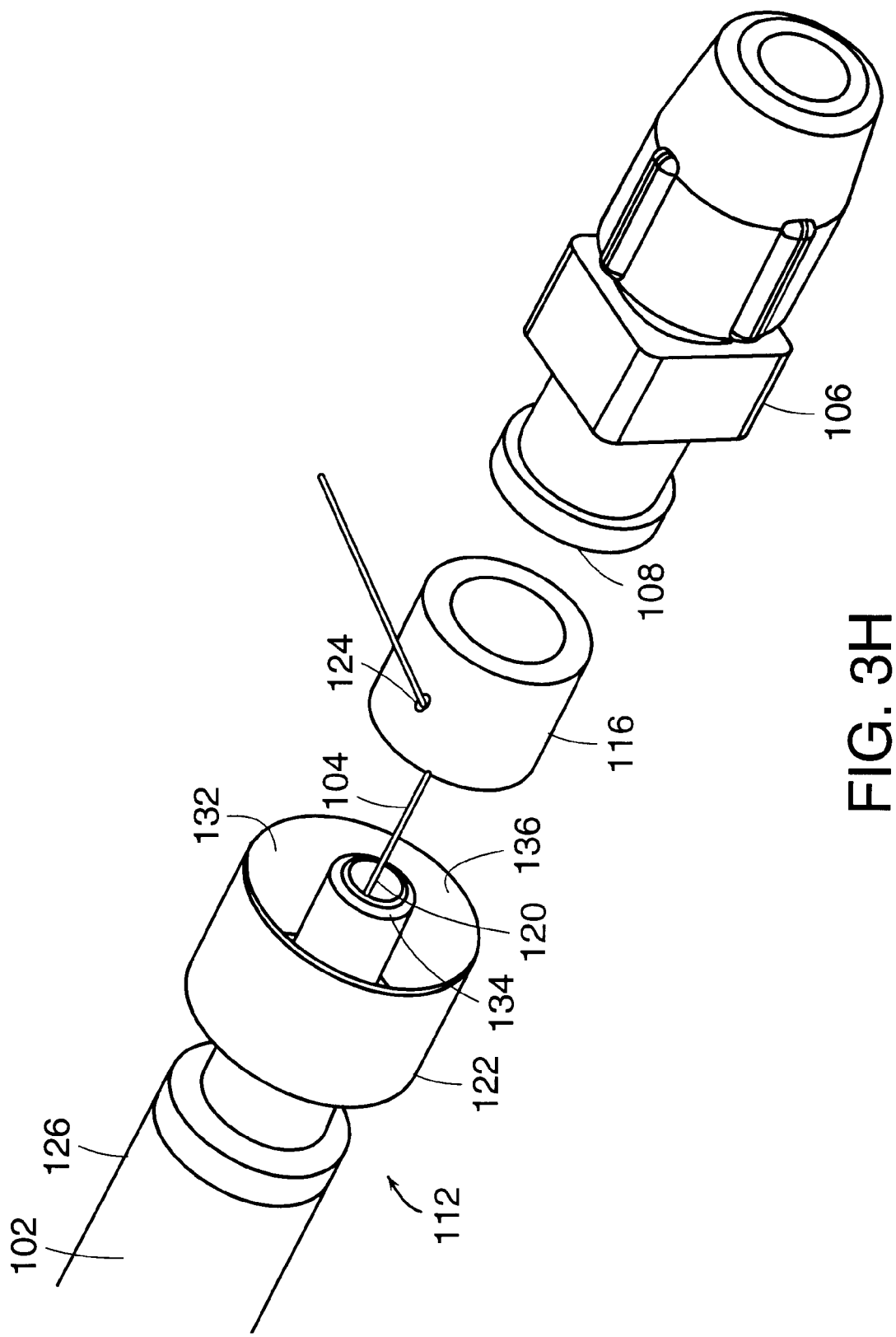

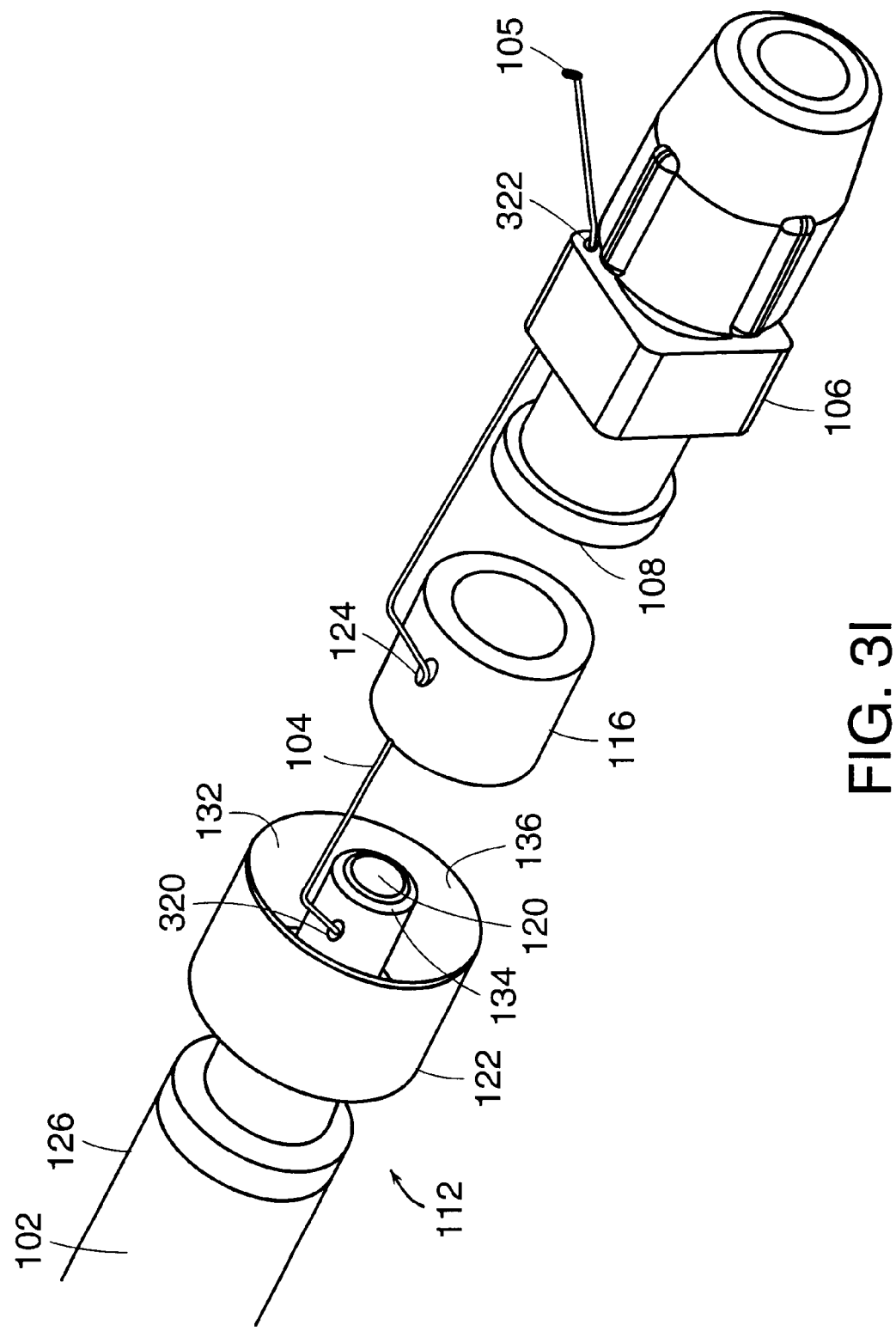

LOCKING CATHETER

CROSS REFERENCE TO RELATED CASE

This claims priority to and the benefit of Provisional U.S. patent application Ser. No. 60/195,931 filed Apr. 10, 2000, the entirety of which is hereby incorporated by reference.

TECHNICAL FIELD

The invention relates generally to catheters and more particularly to pigtail locking catheters.

BACKGROUND INFORMATION

Kidney catheterization and bladder catheterization are medical procedures that permit drainage of the kidney or bladder after surgery or when the urinary system is blocked by an obstruction. Catheters designed for draining the bladder can be inserted percutaneously by first piercing the lower abdominal wall with a large hypodermic needle, fitting a cannula over the needle, and then placing the catheter within the bladder. The kidney can be accessed percutaneously through the middle of the back of the patient. Catheters are also used to drain other viscera such as the abdominal cavity, the stomach, and the biliary system.

To ensure drainage and inhibit movement of the catheter from its placement in a kidney or bladder, a catheter with a pigtail loop at its distal end is often used. After the catheter is inserted into the kidney or bladder, the pigtail loop is formed at a distal section of the catheter by pulling on a proximal end of a suture. The suture extends through and out of the catheter. A proximal portion of the suture is then secured to hold it in place and retain the loop shape at the distal section of the catheter.

One such lockable pigtail loop catheter was available from Boston Scientific Corporation of Natick, Mass. under the name "Microvasive Special Percutaneous Nephrostomy Catheters." With the Special Percutaneous Nephrostomy Catheter, the suture was secured by screwing a separate, loose cap onto the proximal end of the catheter, thereby trapping the suture and securing it. Other locking arrangements also are known.

SUMMARY OF THE INVENTION

The invention relates generally to locking catheters and methods for using such locking catheters. In one aspect, the invention involves a locking catheter. The locking catheter includes an elongated body member which defines a central lumen. The elongated body includes a distal portion and a proximal portion where at least a portion of the elongated body is for placement within a patient. The locking catheter further includes a first proximal member disposed at the proximal portion of the elongated body member and defines a central passageway which extends therethrough and is coaxial with the lumen. The locking catheter further includes an elongated flexible member. The elongated flexible member includes a first end and a second end. The first end is coupled to the distal portion of the elongated body member and extends through both at least a portion of the central lumen of the elongated body member and the central passageway of the first proximal member. The second end is disposed external to the elongated body member. The locking catheter further includes a second proximal member releasably couplable to the first proximal member to allow selective locking and unlocking of the elongated flexible member therebetween. The second proximal member defines a central passageway which extends therethrough and a separate channel which also extends therethrough. The elongated flexible member extends through the separate channel and is slidable therethrough to allow the distal portion of the elongated body member to be drawn toward the proximal portion of the elongated body member to form a loop in the distal portion when the first and second proximal members are decoupled. The central passageway of the second proximal member extends coaxially from the central passageway of the first proximal member and the elongated flexible member is compressed between the first and second proximal members and is non-slidable through the separate channel to secure the loop when the first and second proximal members are coupled together.

In one embodiment the locking catheter further comprises a grommet which defines a central passageway extending therethrough. The grommet is disposed between the first proximal member and the second proximal member with the central passageway of the grommet coaxial with the central passageway of the second proximal member. The grommet creates a seal between the first proximal member and the second proximal member when the first proximal member is coupled to the second proximal member.

In another embodiment, the grommet also defines a channel extending therethrough and the elongated flexible member extends through the channel of the grommet.

In still another embodiment, the first proximal member is a female luer connector and the second proximal member is a male luer connector.

In yet another embodiment, the central lumen of the elongated body member, the central passageway of the first proximal body, and the central passageway of the second proximal body are configured to receive a stylet.

In other embodiments, the elongated member comprises plastic.

In still other embodiments, the elongated member includes a plurality of apertures for allowing fluid to flow into and out of the central lumen of the elongated member.

In yet other embodiments, the first proximal member includes a valve which is open when the first proximal member is coupled to the second proximal member, and which is closed when the first proximal member is decoupled from the second proximal member.

In another embodiment, the first proximal member includes a ratchet and the second proximal member includes teeth. The ratchet engages the teeth when the second proximal member is coupled to the first proximal member and prevents the second proximal member from inadvertently decoupling from the first proximal member.

In another embodiment, the first proximal member includes one of a male and female latch and the second proximal member includes the other of a male and female latch. The male latch includes a prong and the female latch includes a notch. The male latch engages the female latch when the first proximal member is coupled to the second proximal member and prevents the first proximal member from inadvertently decoupling from the second proximal member.

In yet another embodiment, the first proximal member includes a first latch which includes a first set of teeth and the second proximal member includes a second latch which includes a second set of teeth. The first set of teeth engages the second set of teeth when the first proximal member is coupled to the second proximal member and prevents the first proximal member from inadvertently decoupling from the second proximal member.

In still another embodiment, the second proximal member includes a spool to wind the elongated flexible member therearound when the second proximal member is coupled to the first proximal member.

In yet another embodiment, the locking catheter further includes a second elongated body member which defines a central lumen extending therethrough. The elongated body member includes a first port and a second port. The first port is removably couplable to the second proximal member and extends coaxially from the central passageway of the second proximal member. The second port is connectable to a device external to the patient.

In other embodiments, the first port includes a valve for sealing the central passageway of the second proximal member when the second port is decoupled from the device external to the patient. In some embodiments, the valve is a stopcock.

In another aspect, the invention involves a method of locking a catheter in a patient. The method includes providing a locking catheter. The locking catheter includes an elongated body member which defines a central lumen. The elongated body includes a distal portion and a proximal portion where at least a portion of the elongated body member is for placement within a patient. The locking catheter further includes a first proximal member which is disposed at the proximal portion of the elongated body member and defines a central passageway which extends therethrough and is coaxial with the lumen. The locking catheter further includes an elongated flexible member which includes a first end and a second end. The first end is coupled to the distal portion of the elongated body member. The elongated flexible member extends through both at least a portion of the central lumen of the elongated body member and the central passageway of the first proximal member with the second end disposed external to the elongated body member. The locking catheter further includes a second proximal member releasably couplable to the first proximal member to allow selective locking and unlocking of the elongated flexible member therebetween. The second proximal member defines a central passageway extending therethrough and a separate channel also extending therethrough. The elongated flexible member extends through the separate channel and is slidable therethrough to allow the distal portion of the elongated body member to be drawn toward the proximal portion of the elongated body member.

The method further includes inserting at least the distal portion of the elongated body member into the patient and pulling the elongated flexible member through the separate channel of the second proximal member to draw the distal portion of the elongated body member toward the proximal portion of the elongated body member and thereby forming a loop in the distal portion. The method further includes coupling the first and second proximal members together to compress and lock the elongated flexible member and secure the loop.

In still another aspect, the invention involves a locking catheter. The locking catheter includes an elongated body member defining a central lumen and comprising a distal portion and a proximal portion, where at least a portion of the elongated body member is for placement within a patient. The locking catheter further includes a first proximal member disposed at the proximal portion of the elongated body member and defines a central passageway extending therethrough and a separate channel extending therethrough. The central passageway of the first proximal member is coaxial with the lumen. The locking catheter further includes an elongated flexible member. The elongated flexible member includes a first end and a second end. The first end is coupled to the distal portion of the elongated body member and the elongated flexible member extends through at least a portion of the central lumen of the elongated body member, the central passageway of the first proximal member, and the separate channel. The elongated flexible member is slidable through the separate channel to allow the distal portion of the elongated body member to be drawn toward the proximal portion of the elongated body member to form a loop in the distal portion, with the second end disposed external to the elongated body member. The locking catheter further comprises a second proximal member releasably couplable to the first proximal member to allow selective locking and unlocking of the elongated flexible member therebetween. The second proximal member defines a central passageway extending therethrough, and the central passageway of the second proximal member extends coaxially from the central passageway of the first proximal member. The elongated flexible member is compressed between the first and second proximal members and is non-slidable through the separate channel and secures the loop when the first and second proximal members are coupled together.

The foregoing and other objects, aspects, features, and advantages of the invention will become more apparent from the following description, the drawings, and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3A is an illustrative perspective view of a possible arrangement of the components of the lock and the elongated flexible member of the locking-pigtail catheter shown in FIG. 1A.

FIG. 3B is an illustrative perspective view of a possible arrangement of the grommet and the elongated flexible member according to another embodiment of the invention.

FIG. 3C is an illustrative perspective view of a possible arrangement of the grommet and the elongated flexible member according to yet another embodiment of the invention.

FIG. 3D is an illustrative perspective view of a possible arrangement of the grommet and the elongated flexible member according to still another embodiment of the invention.

FIG. 3E is an illustrative perspective view of a possible arrangement of the grommet and the elongated flexible member according to yet another embodiment of the invention.

FIG. 3H is an illustrative perspective pulled-apart view of the male and female luer connectors of the locking-pigtail catheter according to yet another embodiment of the invention.

FIG. 3I is an illustrative perspective pulled-apart view of the male and female luer connectors of the locking-pigtail catheter according to still another embodiment of the invention.

Description

Figure 1A:
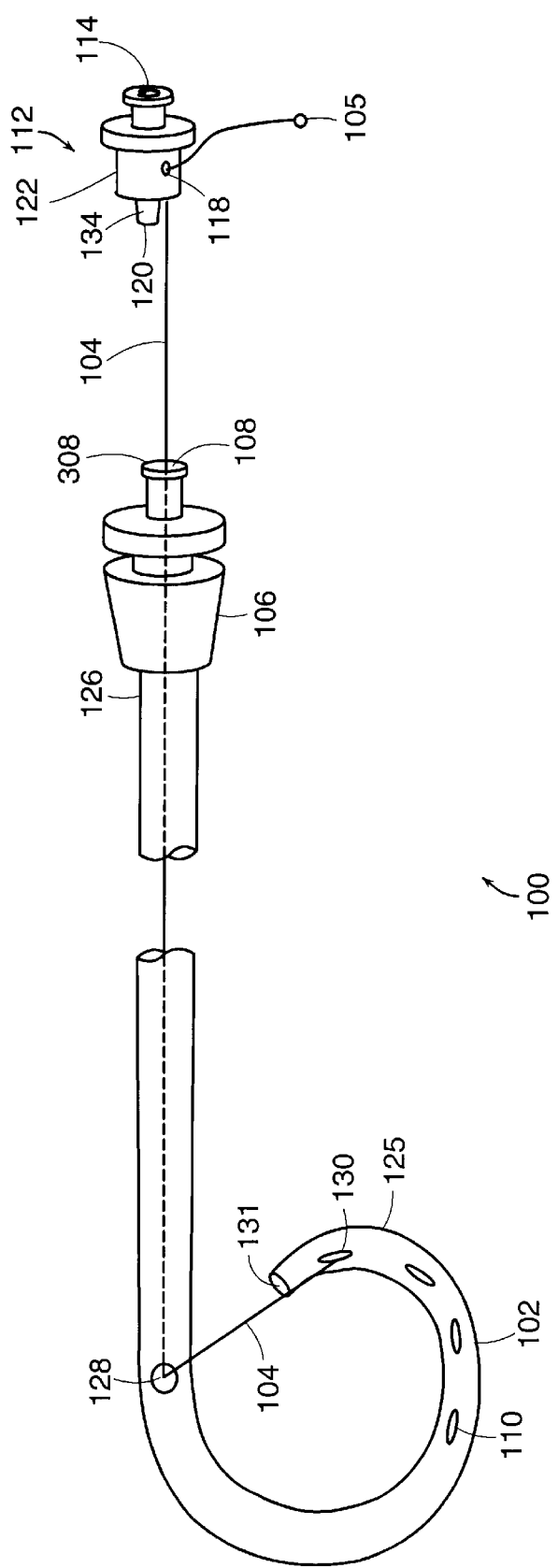
FIG. 1A is an illustrative diagram of a locking-pigtail catheter according to one embodiment of the invention.

The present invention is used to drain viscera such as the kidneys, bladder, abdominal cavity, the stomach, and the biliary system. Referring to FIG. 1A, FIG. 1C, and FIG 1D, in one embodiment, the pigtail-locking catheter 100 includes an elongated body member 102, a female luer connector 106, a male luer connector 112, and an elongated flexible member 104. The elongated body member 102 includes a plurality of apertures 110 disposed along the length of the elongated body member 102 and in the distal portion 125, and a central lumen 131 that extends the entire length of the elongated body member 102. The plurality of apertures 110 provide access to the central lumen 131 to facilitate fluid flow into and/or out of the elongated body member 102. The female luer connector 106 includes an opening 108 and a rim 308. The male luer connector 112 includes an inner wall 134 and a cap 122.

The elongated flexible member 104 is coupled to a distal portion 125 of the elongated body member 102, extends outside of the elongated body member 102 through a distal opening 130, and reenters the elongated body member 102 through another opening 128 disposed in a middle section of the elongated body member 102. The elongated flexible member 104 extends inside the elongated body member 102 through the opening 128 and along the central lumen 131 of the elongated body member 102 to the proximal end 126 of the elongated body member 102. In one embodiment, the elongated flexible member 104 tied to the distal portion 125. In other embodiments, the elongated flexible member 104 can be glued to the distal portion 125 or formed in the distal portion 125.

In another embodiment, the elongated flexible member 104 is coupled to the female luer connector 106 and extends through the elongated body member 102 to the distal portion 125. The elongated flexible member 104 extends outside the elongated body member 102 through the distal opening 130 and reenters the elongated body member 102 through another opening 128 disposed in a middle section of the elongated body member 102. The elongated flexible member 104 extends inside the elongated body member 102 from the opening 128 and along the central lumen 131 of the elongated body member 102 to the proximal end 126 of the elongated body member 102. In other embodiments, the elongated flexible member 104 can be glued to the female luer connector 106 or formed in the female luer connector 106.

Referring to FIGS. 1C and 1D, the distal portion 125 of the elongated body member 102 straightened with a stiffening stylet 166 disposed within the central lumen 131 of the elongated body member 102 is inserted into a patient's bladder, for example, over a guidewire 168. The stiffening stylet 166 and the guidewire 168 are removed from the patient's body leaving the distal portion 125 of the elongated body member 102 disposed within the patient's bladder. The male luer connector 112 is decoupled from the female luer connector 106. The elongated flexible member 104 is pulled through a channel 118 in the male luer connector 112 to draw the distal portion 125 of the elongated body member toward the proximal portion 126 of the elongated body member to form a loop in the elongated body portion 102. As the elongated flexible member 104 is pulled through the channel 118, the male luer connector 112 is moved toward the female luer connector 106 until the male luer connector 112 engages the female luer connector 106. When the male luer connector 112 engages the female luer connector 106, an inner wall 134 of the male luer connector 112 is inserted into an opening 108 of the female luer connector 106. The elongated flexible member 104 is compressed between the rim 308 of the opening 108 and the cap 122 of the male luer connector 112 thereby locking the elongated flexible member 104 in place and locking the distal portion 125 of the elongated body member 102 in the looped position.

Figure 1B:
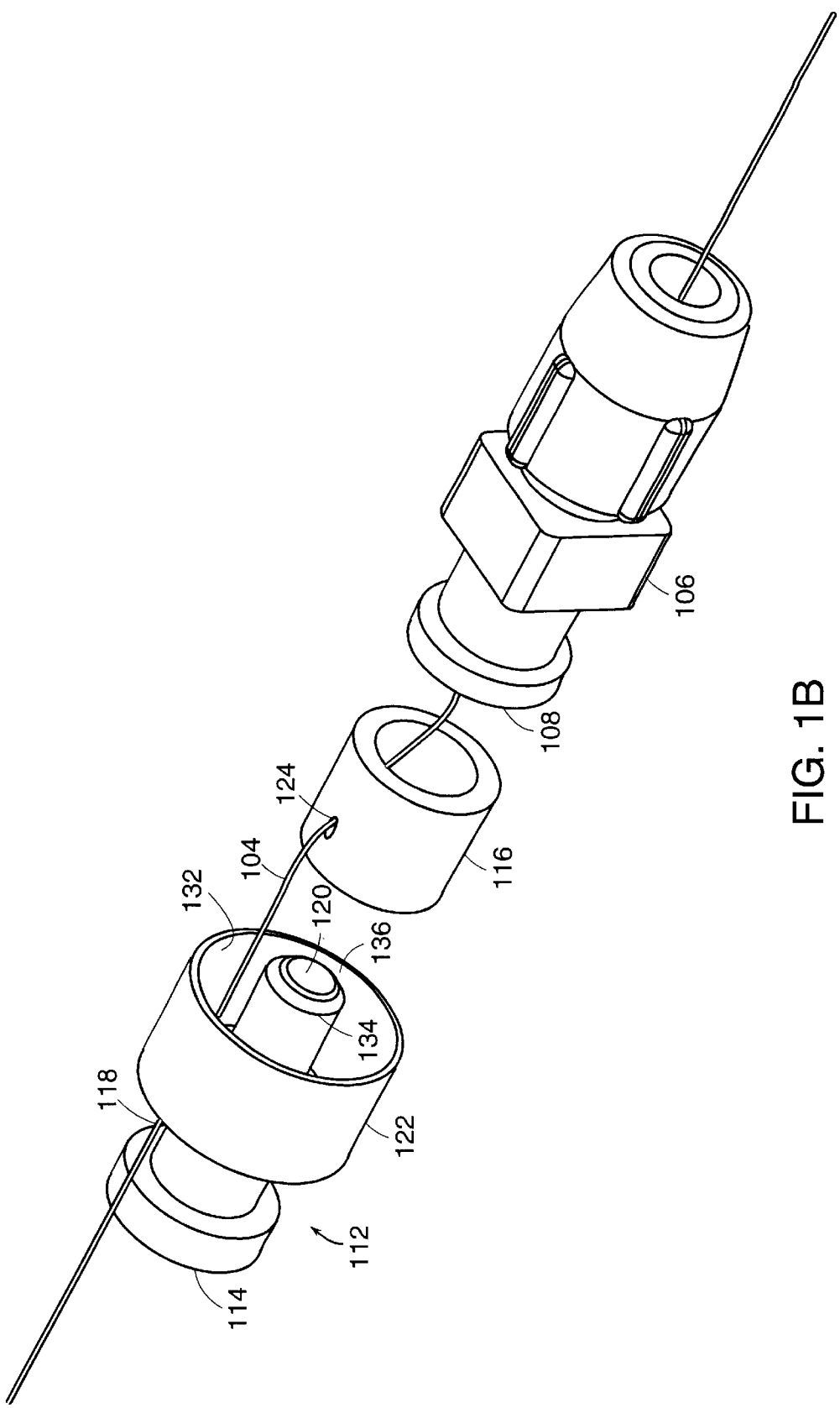
FIG. 1B is an illustrative perspective pulled-apart view of the male and female luer connectors of the locking-pigtail catheter shown in FIG. 1A.
Figure 1C:
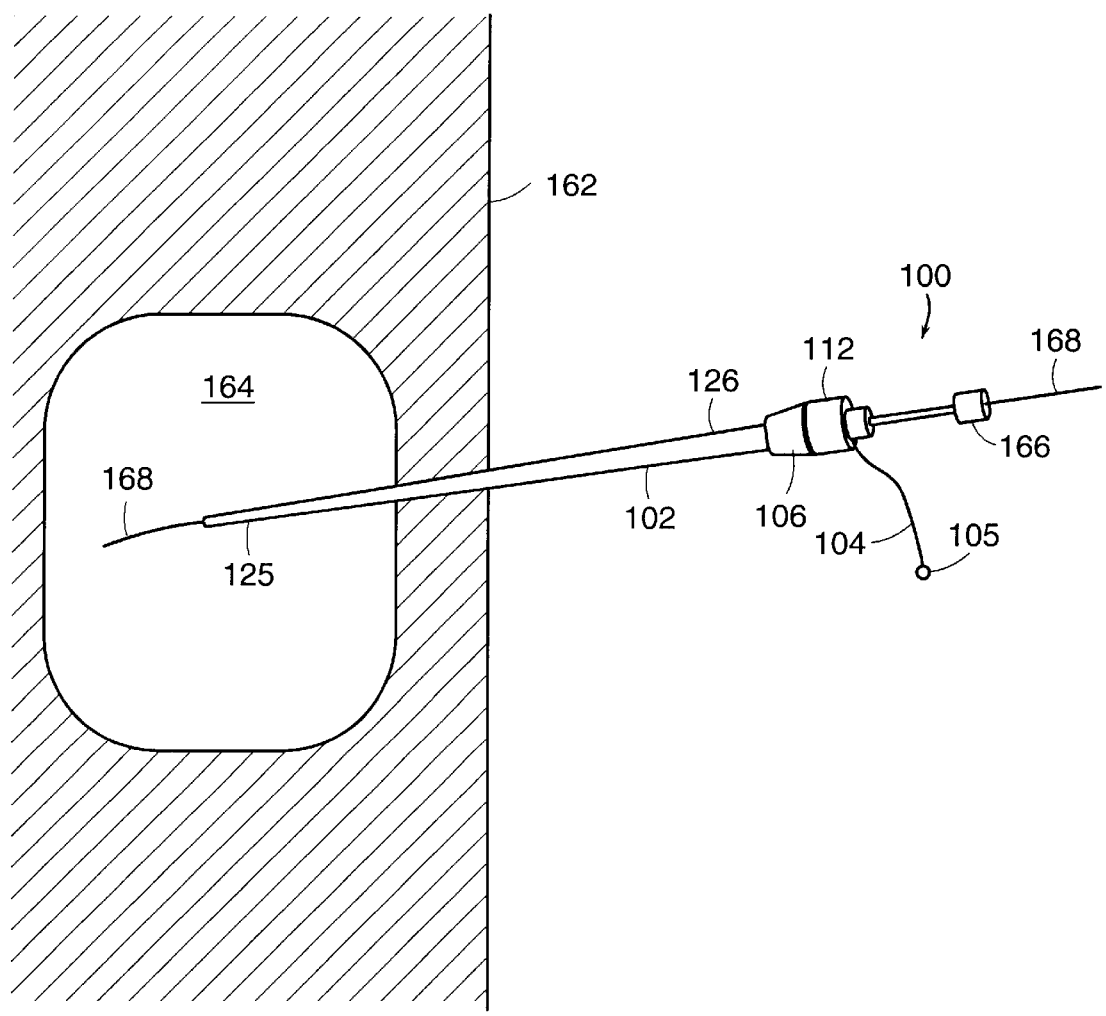
FIG. 1C is an illustrative diagram of the locking-pigtail catheter disposed within a patient in an unlocked position according to one embodiment of the invention.
Figure 1D:
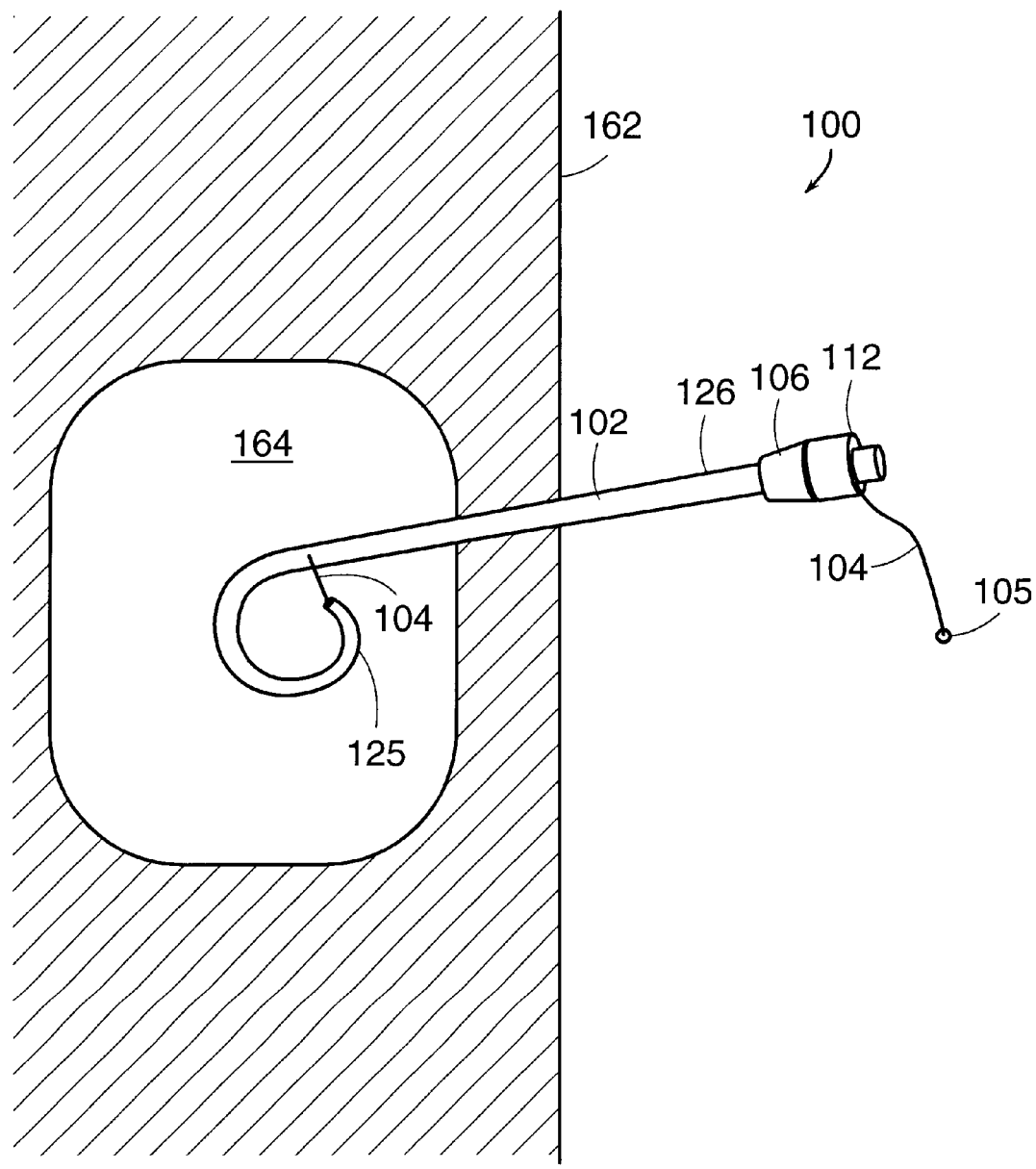
FIG. 1D is an illustrative diagram of the locking-pigtail catheter disposed within a patient in a locked position according to one embodiment of the invention.
Figure 2:
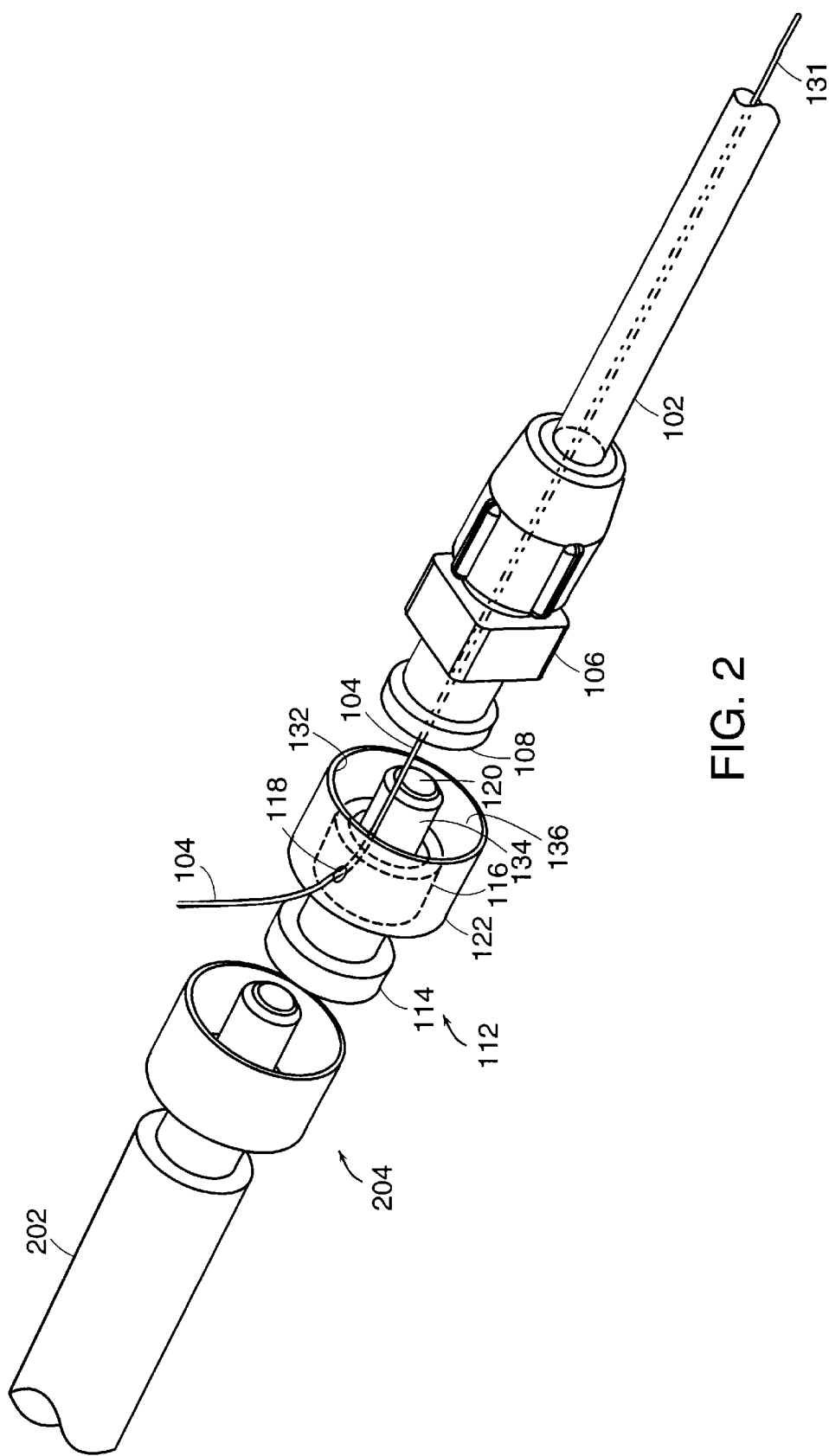
FIG. 2 is an illustrative perspective view of a locking-pigtail catheter and a connection tube according to one embodiment of the invention.

Referring to FIGS. 1A, 1B, and 2, the female luer connector 106 is coupled to the proximal portion 126 of the elongated body member 102 and includes a central passageway that extends therethrough which is coaxial with the central lumen 131 of the elongated body member 102. The elongated flexible member 104 extends through the central passageway of female luer connector 106 and out of a proximal opening 108. In one embodiment, the elongated flexible member 104 is a suture thread made of nylon or other similar material of comparable strength. In other embodiments, the elongated flexible member 104 can be a thread or a flexible metal wire.

The male luer connector 112 includes an inner wall 134 defining a central passageway 120 that extends therethrough, a cap 122 defining a space 132 between the inner wall 134, and a channel 118 located in a wall of the cap 120. The elongated flexible member 104 extends into the space 132 of the male luer connector 112 and exits through the channel 118. The elongated flexible member 104 includes a knot 105 disposed at the proximal end of the elongated flexible member 104 to prevent the elongated flexible member 104 from sliding out of the channel 118 or the male luer connector 112 from being loose or lost. The elongated flexible member 104 slides through the channel 118 and allows the distal portion 125 to be drawn toward the proximal portion 126 to form a loop in the distal portion 125. As the elongated flexible member 104 is drawn through the channel 118, the male luer connector 112 is moved toward the female luer connector 106 until the male luer connector 112 engages the female luer connector 106. When the male luer connector 112 engages the female luer connector 106, the inner wall 134 is inserted into the opening 108 of the female luer connector 106 with the central passageway 120 being coaxial with the central passageway in female luer connector 106. The elongated flexible member 104 is compressed between the rim 308 of the opening 108 and the cap 122 thereby locking the elongated flexible member 104 in place and locking the distal portion 125 of the elongated body member 102 in the pigtail position. By compressing the elongated flexible member 104 between the rim 308 of the opening 108 and the inner wall 134, the elongated flexible member 104 does not interfere with the seal between the male luer connector 112 and the female luer connector 106 when these two parts are coupled together and does not cause wicking along the elongated flexible member 104 and out of the catheter 100.

In one embodiment, the male luer connector 112 and the female luer connector 106 are made of molded biocompatible plastic. In other embodiments, the male luer connector 112 and the female luer connector 106 are made of metal, such as surgical steel or aluminum. In still other embodiments, the male luer connector 112 and the female luer connector 106 need not be used and instead, other similar interference fit connectors can be used that will provide a seal and compress the elongated flexible member 104. The luer connector, male or female, is fitted on the elongated body member 102 by force fitting, gluing, or molding. In some embodiments, the elongated body member 102 can be made of plastic, nylon, polyethylene, ethylene-vinyl acetate co-polymer, or similar material.

Referring to FIGS. 1B, 2, and 3A, in another embodiment, a grommet 116 made of compressible material is placed inside the space 132 of the cap 122 surrounding the inner wall 134. When the male luer connector 112 engages the female luer connector 106, the grommet 116 is compressed between the rim 308 of the opening 108 and the cap 122 and creates a seal between the male luer connector 112 and the female luer connector 106. As shown in FIGS. 1B and 3A, the elongated flexible member 104 may radially extend through a channel 124 in the grommet 116. When the male luer connector 112 engages the female luer connector 106, the grommet 116 is compressed and the grommet 116 thereafter compresses the elongated flexible member 104 (as shown in FIG. 4) thereby locking the elongated flexible member 104 in place and locking the distal portion 125 of the elongated body member 102 in the pigtail position.

The elongated flexible member 104 may also be compressed and thereby locked by the grommet 116 in a variety of ways. Referring to FIG. 3B, in one embodiment, the elongated flexible member 104 extends through the central passageway 302 of the grommet 116 and is compressed between the interior surface 310 of the grommet 116 and the exterior surface of inner wall 134. Referring to FIG. 3C, in another embodiment, the elongated flexible member 104 extends between and is compressed by the exterior surface 312 of the grommet 116 and an interior surface 136 of the cap 122. Referring to FIG. 3D, in still another embodiment, the elongated flexible member 104 extends longitudinally through the wall of the grommet 116. When the grommet 116 is compressed, the elongated flexible member 104 is compressed. Referring to FIG. 3E, in yet another embodiment, the elongated flexible member 104 is compressed between the distal face 306 of the grommet 116 and the rim 308 of the female luer connector 106. In one embodiment, the grommet 116 is made of latex. In other embodiments, the grommet 116 can be made of silicone or foam.

The benefit of using the grommet 116 between the male luer connector 112 and the female luer connector 106 is that a better seal is created between the male luer connector 112 and the female luer connector 106, wicking is prevented in the case where the elongated flexible member 104 is inadvertently compressed between the male luer connector 112 and the female luer connector 106, and the elongated flexible member 104 is held more securely thereby maintaining the loop in the distal portion 125 of the elongated body member 102.

Figure 3F:
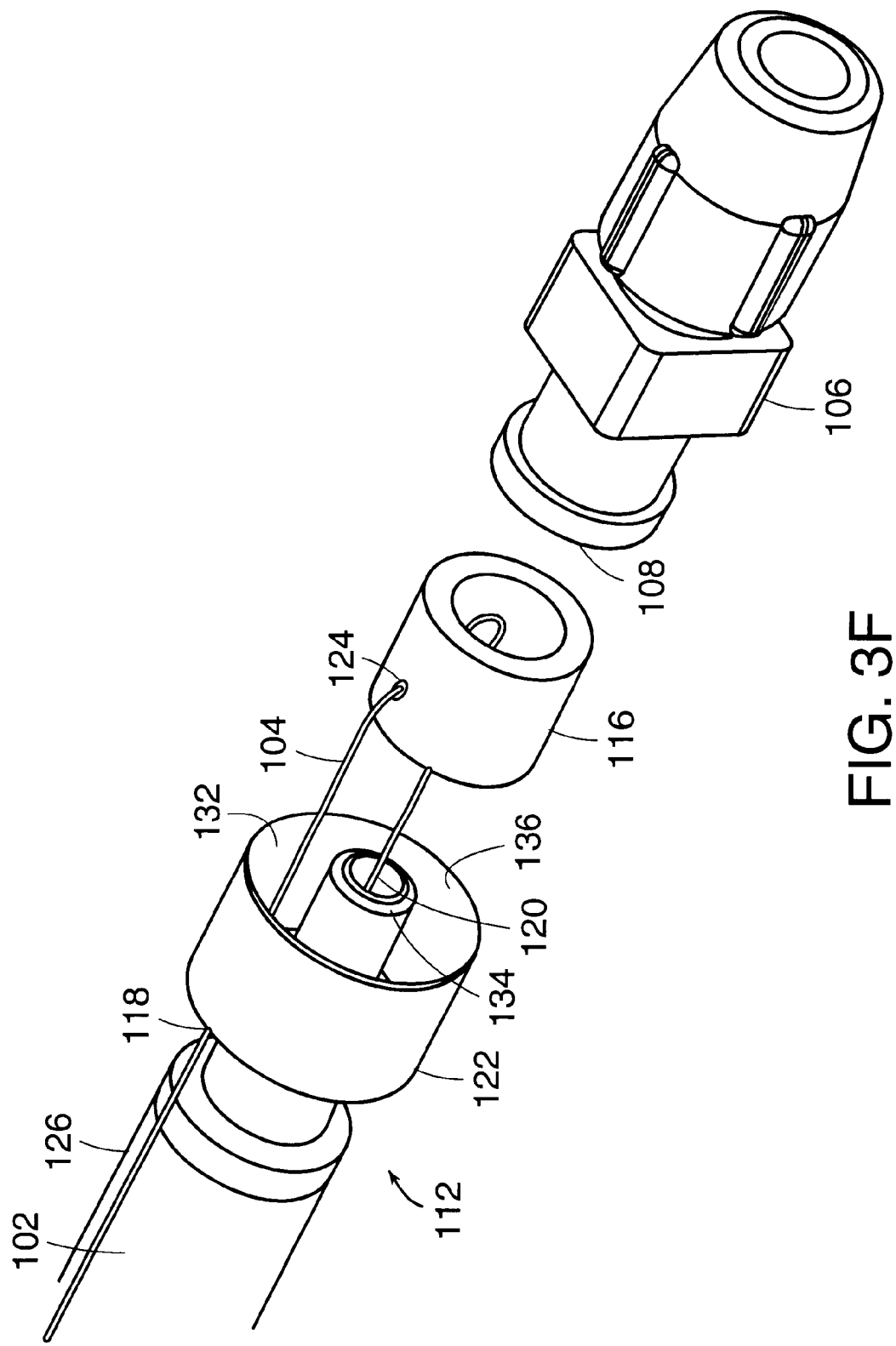
FIG. 3F is an illustrative perspective pulled-apart view of the male and female luer connectors of the locking-pigtail catheter according to another embodiment of the invention.
Figure 3G:
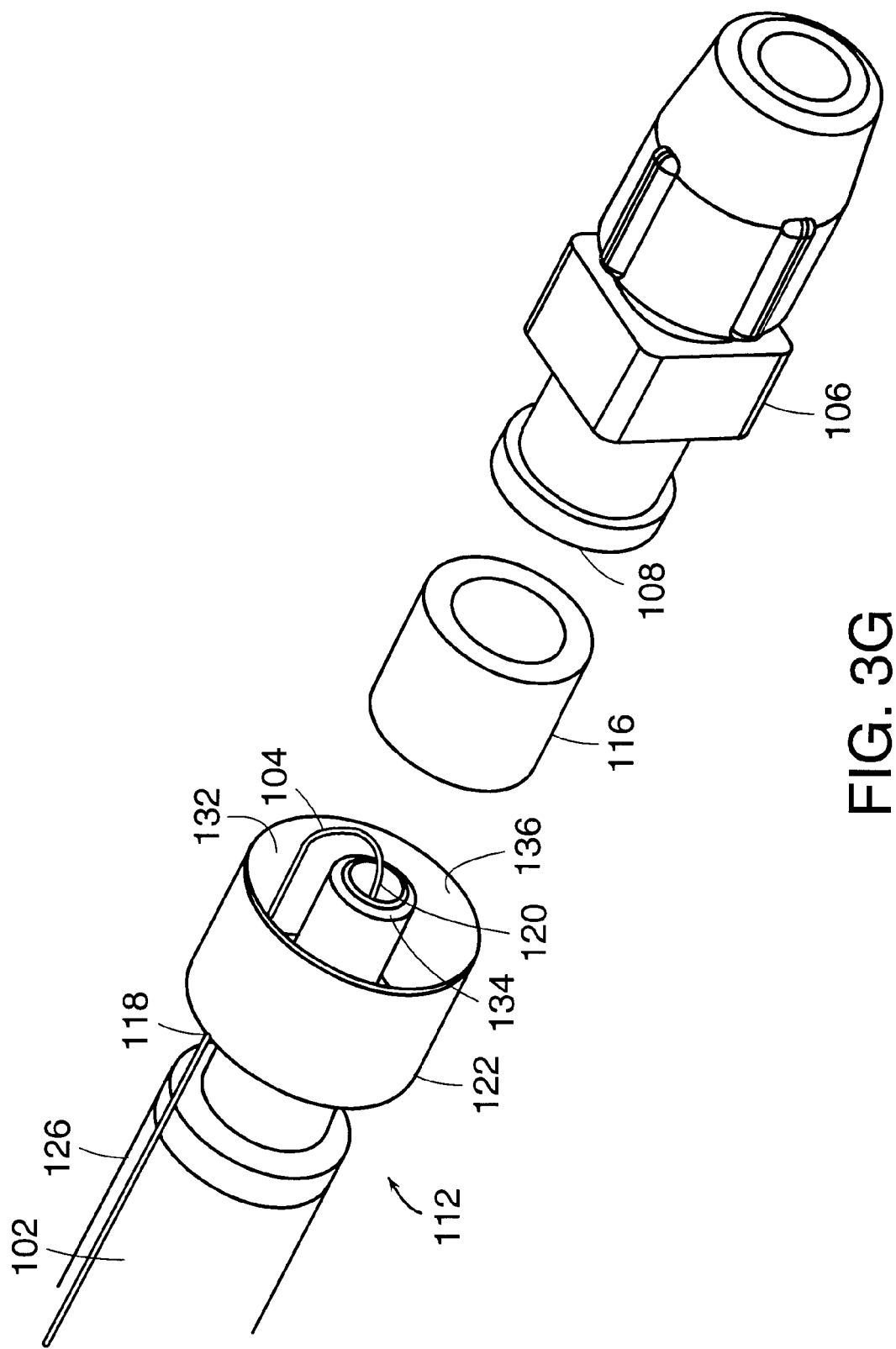
FIG. 3G is an illustrative perspective pulled-apart view of the male and female luer connectors of the locking-pigtail catheter according to still another embodiment of the invention.
Figure 4:
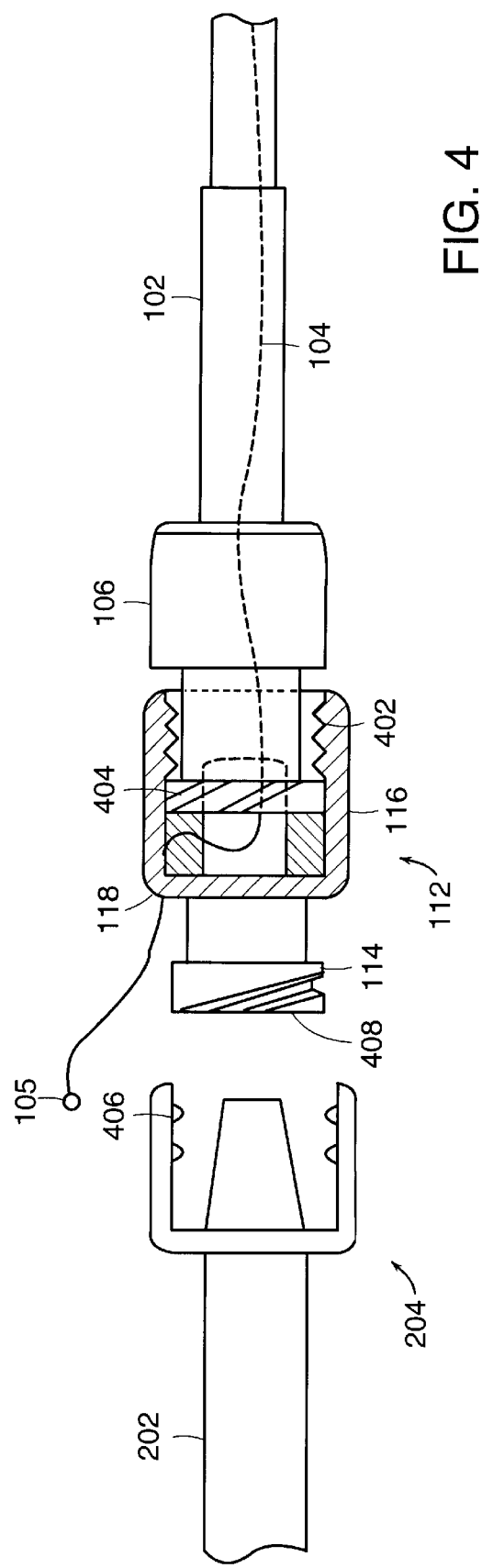
FIG. 4 is an illustrative diagram in partial longitudinal cross-section of a coupled male and female luer connector according to one embodiment of the invention.

Referring to FIGS. 3F, 3G, and 3H, the positions of the female luer connector 106 and the male luer connector 112 may be reversed. In such embodiments, the male luer connector 112 is coupled to the proximal portion 126 of the elongated body member 102, and the female luer connector 106 is releasably couplable to the male luer connector 112. The elongated flexible member 104 may also be compressed and thereby locked by the grommet 116 in a variety of ways as shown in FIGS. 3F, 3G, and 3H.

Referring to FIG. 3I, in another embodiment, the elongated flexible member 104 exits the central passageway 120 of the male luer connector 112 through an opening 320 in the inner wall 134. The elongated flexible member 104 pass through the channel 124 in the grommet 116 and then passes through a passageway 322 in the female luer connector 106.

Referring again to FIGS. 1A and 2, the male luer connector 112 includes proximally a female luer portion 114 which is used to mate with a male luer connector 204 of a connection tube 202. The connection tube 202 is used to connect the locking-pigtail catheter 100 with a medical device such as a collecting bag, for example.

Referring to FIG. 4, typically, the male luer connector 112 and the female luer connector 106 are threaded and are held together when the threads 402 of the male luer connector 112 engage the threads 404 of the female luer connector 106. The male luer connector 204 of connection tube 202 and the female luer portion 114 of the male luer connector 112 are also similarly threaded. The male luer connector 204 and the female portion 114 are held together when the threads 406 of the male luer connector 204 engage the threads 408 of the female luer portion 114. When a patient attempts to disconnect the connection tube 202 from the locking-pigtail catheter 100, the patient may accidentally disengage the male luer connector 112 from the female luer connector 106 instead of disengaging the male luer connector 204 from the female portion 114 and thereby unlock the loop in the distal portion 125 and increase the risk of dislodging the catheter 100 from the body cavity. To prevent the male luer connector 112 from being inadvertently disengaged from the female luer 106, various safety features may be incorporated into the male luer connector 112 and the female luer connector 106 and are discussed below.

Figure 5:
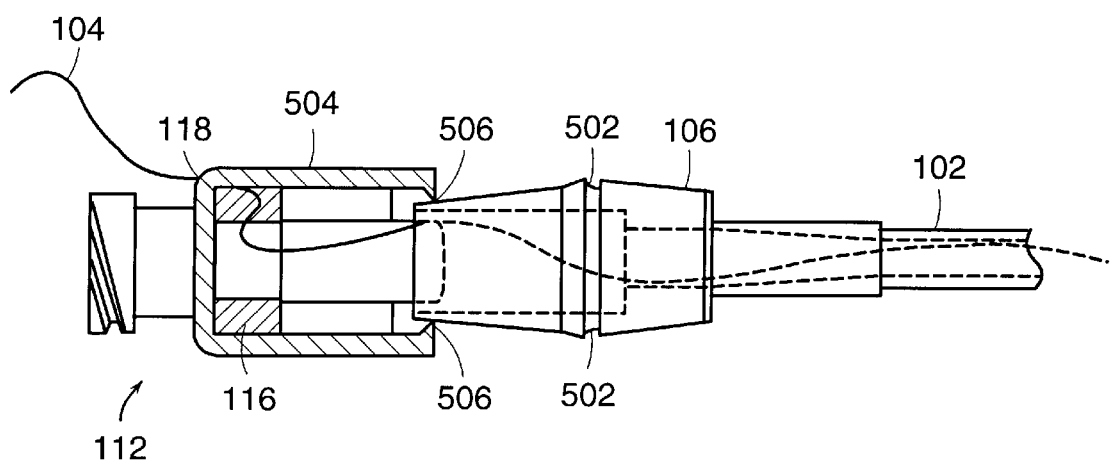
FIG. 5 is an illustrative diagram in partial longitudinal cross-section of a coupled male and female luer connector with a mechanism to prevent inadvertent decoupling according to one embodiment of the invention.

Referring to FIG. 5, in one embodiment the male luer connector 112 includes a cap 504 which includes one or more prongs 506. The female luer connector 106 includes one or more notches 502. When the male luer connector 112 and the female luer connector 106 engage each other (by pushing or screwing them together, for example), the prongs 506 engage the notch 502 and prevent further rotational motion of the male luer connector 112 or the female luer connector 106 and the male luer connector 112 from being inadvertently disconnected from the female luer connector 106. The male luer connector 112 can only be disengaged from the female luer connector 106 when the cap 504 is squeezed radially and simultaneously at two diametrically opposed positions disposed at a ninety-degree angle from the prongs 506 thereby causing the prongs 506 to lift out of the notch 502. Alternatively, the notch 502 and the prongs 506 may extend circumferentially, and fitting and release may be done through rigorous pushing together and pulling apart. When the notch 502 is circumferential groove, the male luer connector 112 freely rotates in either a clockwise or counterclockwise direction.

Figure 6:
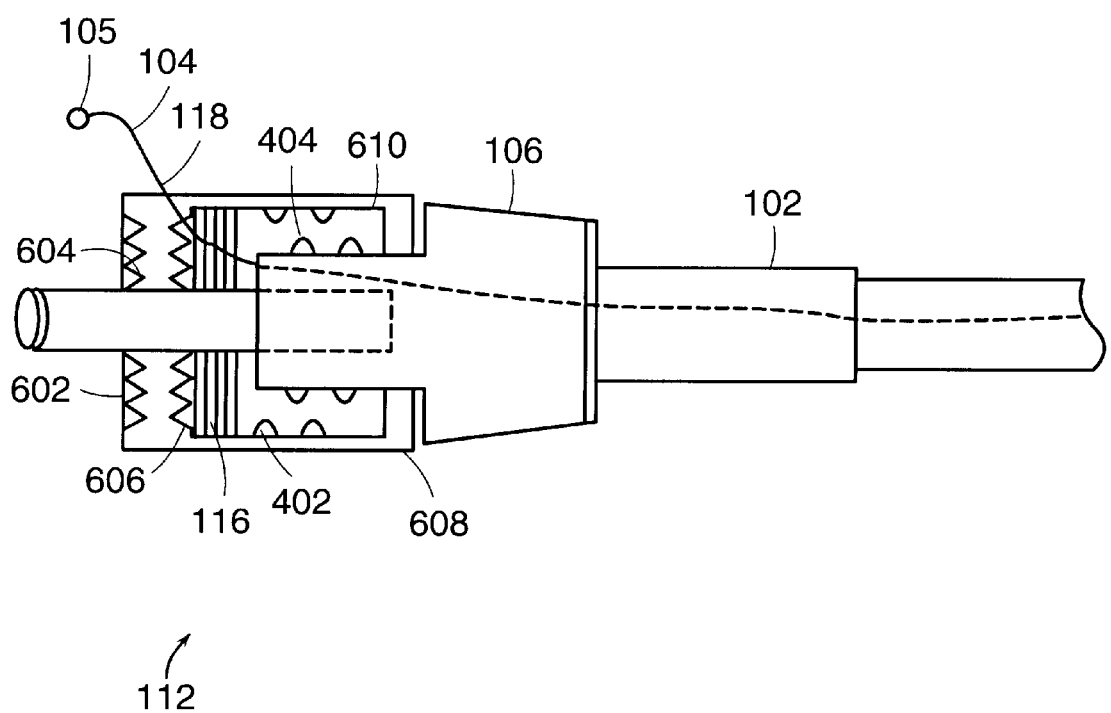
FIG. 6 is an illustrative diagram in partial longitudinal cross-section of a coupled male and female luer connector with a mechanism to prevent inadvertent decoupling according to another embodiment of the invention.

Referring to FIG. 6, in another embodiment, the cap 602 includes an outside portion 608 and an inside portion 610. The outside portion 608 includes teeth 604 disposed on the inside proximal face and extending longitudinally. The inside portion 610 includes teeth 606 disposed on the outside proximal face and extending longitudinally but in the opposite direction of teeth 604. When the male luer connector 112 and the female luer connector 106 engage each other by screwing them together, the teeth 604 engage the teeth 606 and allow the outer portion 608 to turn the inner portion 610 and thereby tighten the coupling of the male luer connector 112 and the female luer connector 106. The outer portion 608 spins freely in the opposite (loosening) direction which prevents the male luer connector 112 from being inadvertently unscrewed and disconnected from the female luer connector 106. The male luer connector 112 can only be disengaged from the female luer connector 106 when the cap 602 is pressed toward the female luer connector 106 and turned in the loosening direction at the same time. Pressing the cap 602 toward the female luer connector 106 causes the outer portion 608 to move toward the inner portion 610 which causes the teeth 604 to engage the teeth 606 and allows the outer portion 608 to turn the inner portion 610 in the loosening direction.

Figure 7A:
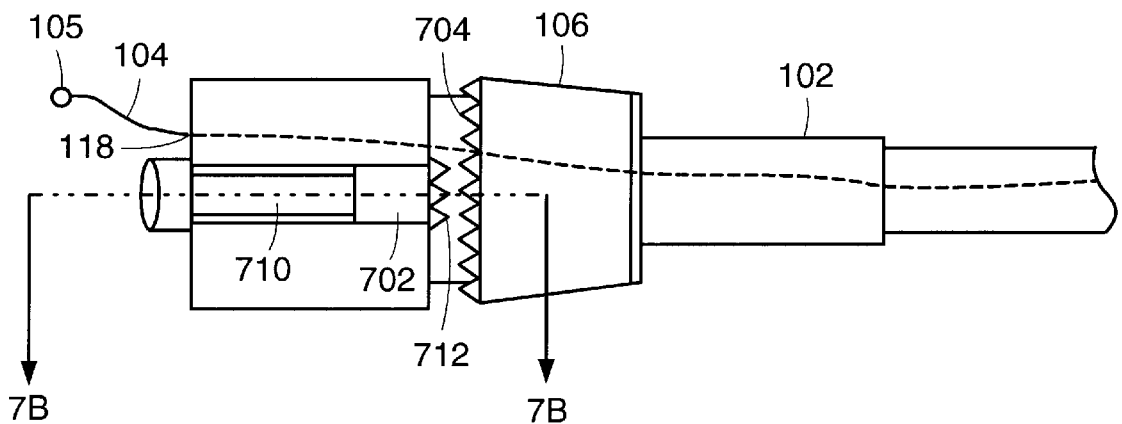
FIG. 7A is an illustrative diagram of a coupled male and female luer connector with a mechanism to prevent inadvertent decoupling according to yet another embodiment of the invention.
Figure 7B:
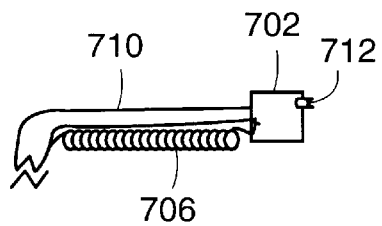
FIG. 7B is an illustrative diagram in partial longitudinal cross-section of the mechanism to prevent inadvertent decoupling shown in FIG. 7A.

Referring to FIGS. 7A and 7B, in still another embodiment, the cap 708 includes a spring-loaded slidable ratchet 702 with a spring 706 and the slidable ratchet 702 mounted over a slide 710. The female luer connector 106 includes teeth 704 disposed on a proximal face and extending longitudinally. When the male luer connector 112 and the female luer connector 106 engage each other by screwing them together, the teeth 712 in the spring-loaded ratchet 702 engage the teeth 704 and prevent the male luer connector 112 from being inadvertently unscrewed and disconnected from the female luer connector 106. The male luer connector 112 can only be disengaged from the female luer connector 106 when the spring-loaded ratchet 702 is pressed proximally so that the teeth 704 and 712 disengage while male luer connector 112 is turned.

Figure 7E:
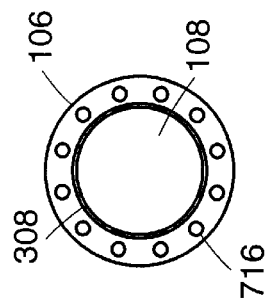
FIG. 7E is an illustrative top view diagram of the female luer connector portion of the mechanism to prevent inadvertent decoupling shown in FIG. 7C.
Figure 7C:
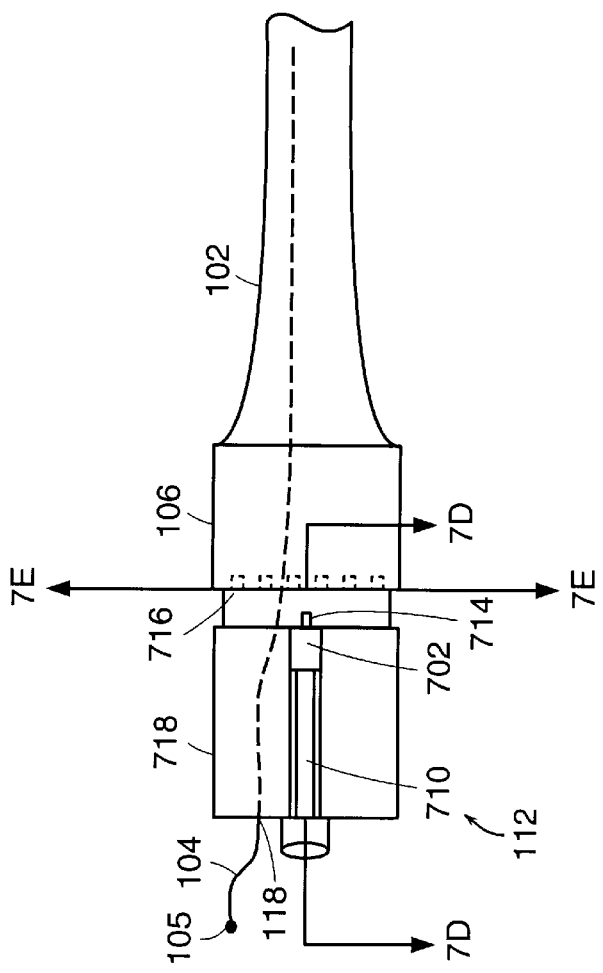
FIG. 7C is an illustrative diagram of a coupled male and female luer connector with a mechanism to prevent inadvertent decoupling according to another embodiment of the invention.
Figure 7D:
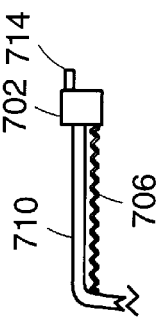
FIG. 7D is an illustrative diagram in partial longitudinal cross-section of the mechanism to prevent inadvertent decoupling shown in FIG. 7C.

Referring to FIGS. 7C, 7D, and 7E, in still another embodiment, the cap 718 includes a spring-loaded slidable ratchet 702 with a spring 706 and the slidable ratchet 702 mounted over a slide 710. The female luer connector 106 includes holes (or notches) 716 disposed on a proximal face. When the male luer connector 112 and the female luer connector 106 engage each other by screwing them together, the pin 714 in the spring-loaded ratchet 702 engages one of the holes 716 and prevents the male luer connector 112 from being inadvertently unscrewed and disconnected from the female luer connector 106. The male luer connector 112 can only be disengaged from the female luer connector 106 when the spring-loaded ratchet 702 is pressed proximally so that the pin 714 disengages from one of the holes 716 while male luer connector 112 is turned.

Figure 8:
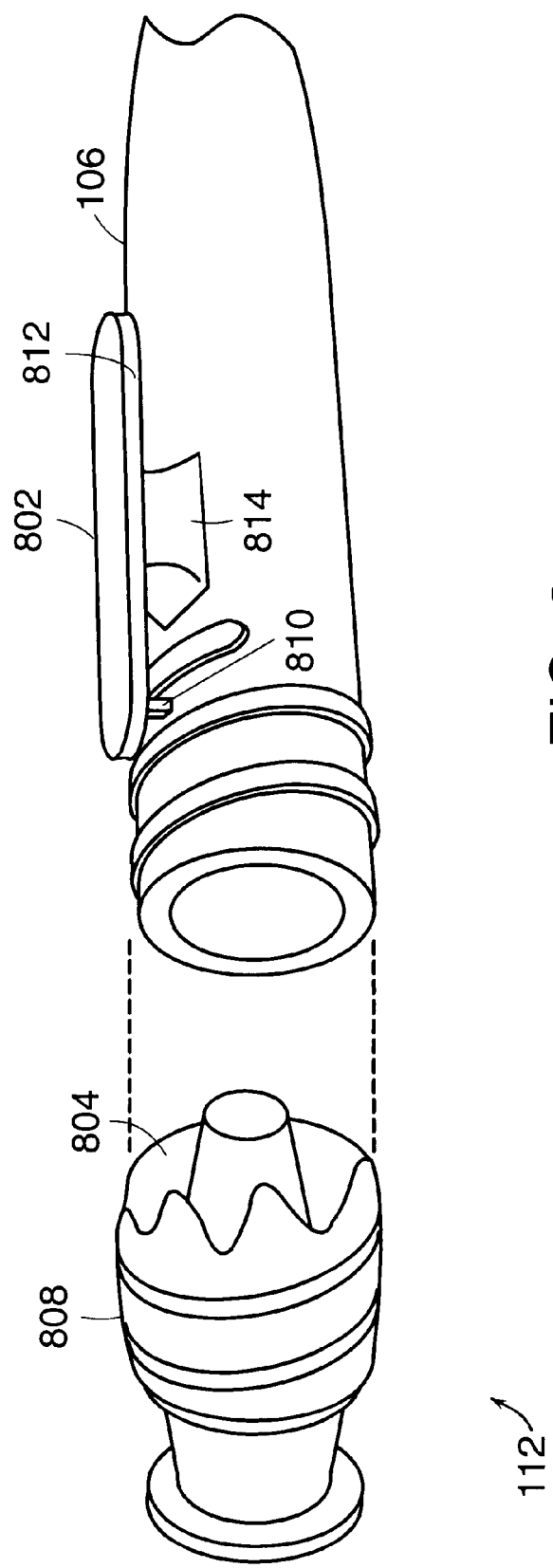
FIG. 8 is an illustrative diagram in partial longitudinal cross-section of a decoupled male and female luer connector with a mechanism to prevent inadvertent decoupling according to still another embodiment of the invention.

Referring to FIG. 8, in yet another embodiment, the cap 808 includes teeth 804, and the female luer connector 106 includes a flexible but resilient ratchet 802 which includes a tongue 810, a landing 812, and a pivot 814. When the male luer connector 112 and the female luer connector 106 engage each other by screwing them together, the tongue 810 engages the teeth 804 and prevents the male luer connector 112 from being inadvertently unscrewed and disconnected from the female luer connector 106. The male luer connector 112 can only be disengaged from the female luer connector 106 when the landing 812 is pressed down radially thereby causing the tongue 810 to raise (outwardly via pivot 814) and then turning the male luer connector 112.

Figure 9:
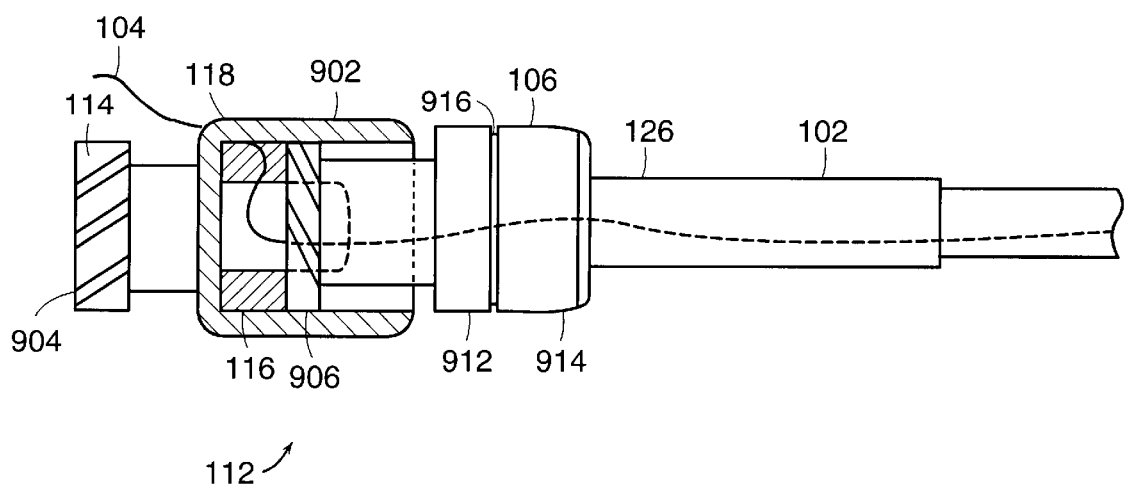
FIG. 9 is an illustrative diagram in partial longitudinal cross-section of a male and female luer connector with a mechanism to prevent inadvertent decoupling according to another embodiment of the invention.

Referring to FIG. 9, in yet another embodiment, the female luer connector 106 includes right-hand threads 906 and the female portion 114 of the male luer connector 112 includes left-hand threads 904. The male luer connector 112 and the female luer connector 106 engage each other by screwing together in one direction, and the male luer connector 204 on the connection tube 202 and the female portion 114 engage each other by screwing together in the opposite direction. When the connection tube 202 is disconnected from the female portion 114 of the male luer connector 112, the male luer connector 204 is turned in a direction that tightens the connection between the male luer connector 112 and the female luer connector 106, thus preventing the male luer connector 112 from being inadvertently unscrewed and disconnected from the female luer connector 106 and releasing the elongated flexible member 104.

In another embodiment, the female luer connector 106 includes a rotatable connector 910 coupled to the proximal portion 126 of the elongated body member 102. The rotatable connector 910 includes a first rotating portion 912, a second rotating portion 914 coaxial with the first rotating portion 912, and rotation point 916 coaxial with rotating portions 912 and 914. Rotating portion 912 and 914 are independently rotatable in both the clockwise and counter-clockwise directions. The male luer connector 112 and the female luer connector 106 are coupled together by screwing the male luer connector 112 to the female luer connector 106 while holding the rotating portion 912. After the male luer connector 112 and the female luer connector 106 are coupled together, the male luer connector 112 and the female luer connector 106 will rotate freely about the rotating point 916, The male luer connector 112 can only be disengaged from the female luer connector 106 by holding the rotating portion 912 while unscrewing the male luer connector 112. Inadvertently holding any other portion besides rotating portion 912 will prevent decoupling of the male luer connector 112 and the female luer connector 106.

Figure 10A:
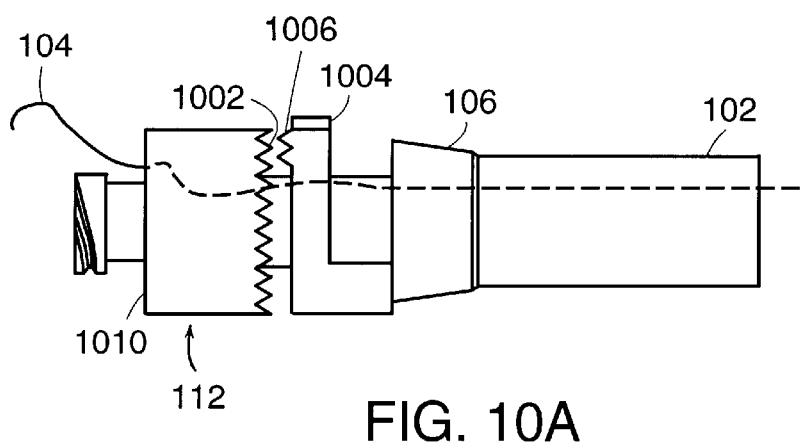
FIG. 10A is an illustrative diagram of a coupled male and female luer connector with a mechanism to prevent inadvertent decoupling in an unengaged position according to another embodiment of the invention.
Figure 10B:
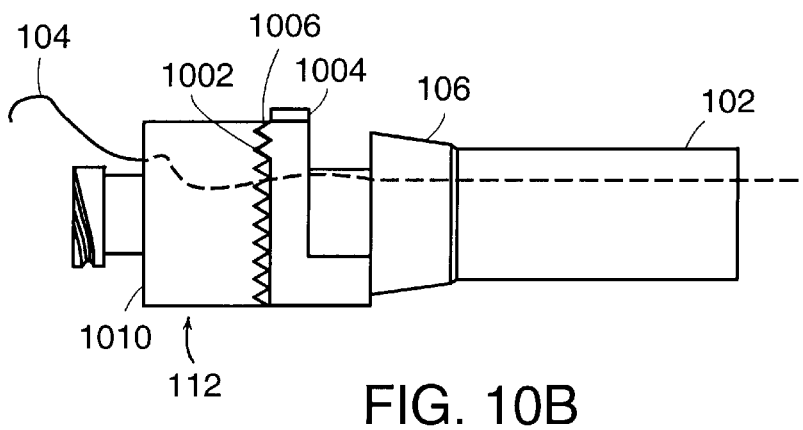
FIG. 10B is an illustrative diagram of a coupled male and female luer connector with the mechanism to prevent inadvertent decoupling shown in FIG. 10A in an engaged position.
Figure 10C:
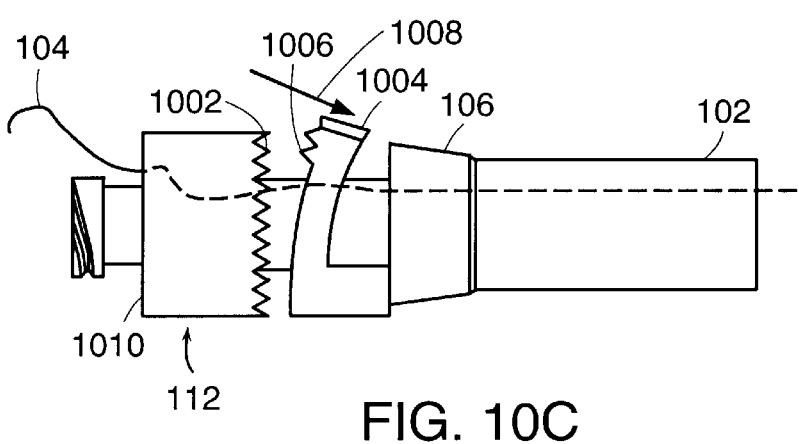
FIG. 10C is an illustrative diagram of the mechanism to prevent inadvertent decoupling shown in FIGS. 10A and 10B being disengaged.

Referring to FIGS. 10A, 10B, and 10C, in another embodiment, The cap 1010 includes teeth 1002 extending longitudinally from a distal face, and the female luer connector 106 includes a compressible member 1004 which includes teeth 1006. When the male luer connector 112 and the female luer connector 106 engage each other by screwing them together, the teeth 1002 engage the teeth 1006 and prevent the male luer connector 112 from being inadvertently unscrewed and disconnected from the female luer connector 106. The male luer connector 112 can only be disengaged from the female luer connector 106 when the compressible member 1004 is compressed in a direction indicated by arrow 1008. Compressing the compressible member 1004 causes the teeth 1002 to disengage the teeth 1006 and allows the male luer connector 112 and the female luer connector 106 to be unscrewing.

In other embodiments, other safety locking mechanisms can be used to prevent the male luer connector 112 from being inadvertently unscrewed and disconnected from the female luer connector 106 and releasing the elongated flexible member 104. Additionally, all the components of the safety locking mechanisms previously described above that are part of the male luer connector 112 can be instead part of the female luer connector 106. Likewise, all the components of the safety locking mechanisms that are part of the female luer connector 106 can be instead part of the male luer connector 112.

In another embodiment, a stopcock valve is connected to and located between the connection tube 202 and the female portion 114 of the male luer connector 112. The stopcock valve is used to prevent leaking from the locking-pigtail catheter 100 when the connection tube 202 is disconnected from the female portion 114 or from a medical device.

Figure 11A:
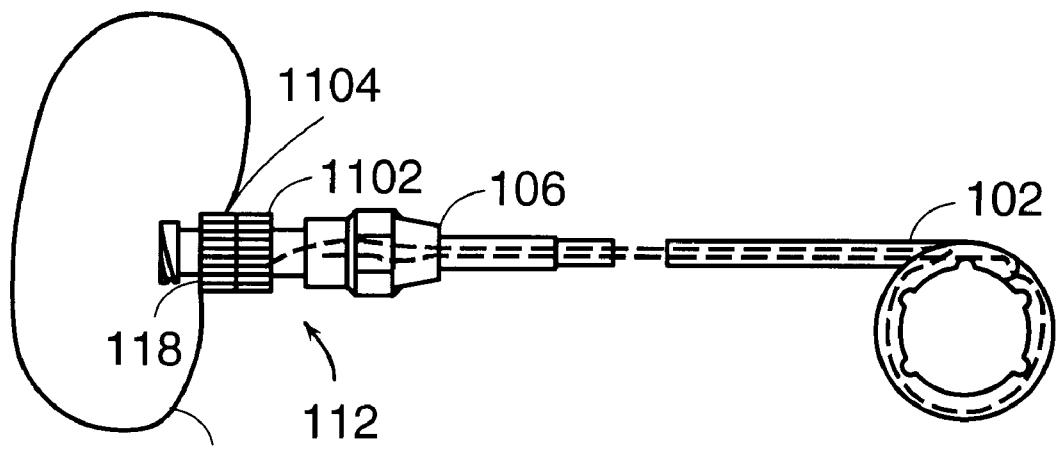
FIG. 11A is an illustrative diagram of a locking-pigtail catheter including a spool according to one embodiment of the invention.
Figure 11B:
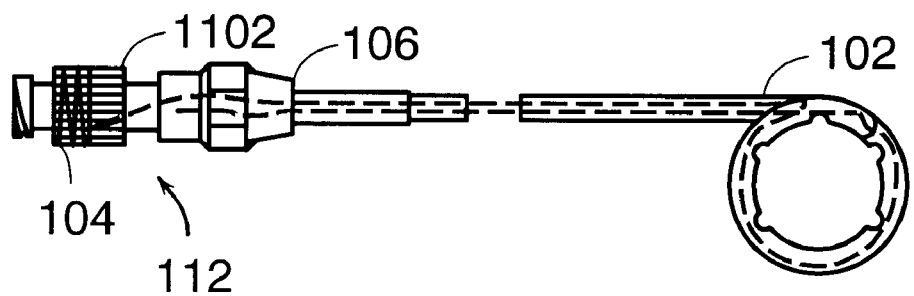
FIG. 11B is an illustrative diagram a suture wound around the spool of the locking-pigtail catheter shown in FIG. 11A.

Referring to FIGS. 11A and 11B, in still another embodiment, the male luer connector 112 includes a spool 1102 for winding any excess elongated flexible member 104 extending out of the channel 118 of the male luer connector 112 when the male luer connector 112 is coupled to the female luer connector 106. The end 1104 of the elongated flexible member 104 is coupled to spool 1102. As the spool 1102 is turned, the elongated flexible member 104 is wound around the spool 1102. Additionally, the spool 1102 can include a ratchet which prevents the spool 1102 from unwinding unless the ratchet is released, by pushing or pulling the spool 1102 longitudinally, for example. In another embodiment, the spool 1102 may be a circumferential groove disposed in the male luer connector 112 with a slit in the side of the groove to secure the end 1104 of the elongated flexible member 104.

In yet another embodiment, the female luer connector 106 includes a valve disposed in the central passageway of the female luer connector 106. The valve is closed when the male luer connector 112 is decoupled from the female luer connector 106. When the male luer connector 112 engages the female luer connector 106, the inner wall 134 is inserted into the opening 108 of the female luer connector 106 thereby opening the valve disposed in the central passageway in female luer connector 106.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A locking catheter, comprising:
an elongated body member defining a central lumen and comprising a distal portion and a proximal portion, at least a portion of the elongated body member for placement within a patient;
a first proximal member disposed at the proximal portion of the elongated body member and defining a central passageway extending therethrough and coaxial with the lumen;
an elongated flexible member comprising a first end and a second end, the first end coupled to the distal portion of the elongated body member, the elongated flexible member extending through both at least a portion of the central lumen of the elongated body member and the central passageway of the first proximal member with the second end disposed external to the elongated body member; and
a second proximal member releasably couplable to the first proximal member to allow selective locking and unlocking of the elongated flexible member therebetween, the second proximal member defining a central passageway extending therethrough and a separate channel extending therethrough, the elongated flexible member extending through the separate channel and being slidable therethrough to allow the distal portion of the elongated body member to be drawn toward the proximal portion of the elongated body member to form a loop in the distal portion when the first and second proximal members are decoupled, the central passageway of the second proximal member extending coaxially from the central passageway of the first proximal member and the elongated flexible member being compressed between the first and second proximal members and non-slidable through the separate channel to secure the loop when the first and second proximal members are coupled together.

2. The locking catheter of claim 1, further comprising a grommet defining a central passageway extending therethrough, the grommet disposed between the first proximal member and the second proximal member with the central passageway of the grommet coaxial with the central passageway of the second proximal member and creating a seal between the first proximal member and the second proximal member when the first proximal member is coupled to the second proximal member.

3. The locking catheter of claim 2, wherein the grommet also defines a channel extending therethrough and wherein the elongated flexible member extends through the channel of the grommet.

4. The locking catheter of claim 1, wherein the first proximal member is a female luer connector and the second proximal member is a male luer connector.

5. The locking catheter of claim 1, wherein central lumen of the elongated body member, the central passageway of the first proximal body, and the central passageway of the second proximal body are configured to receive a stylet.

6. The locking catheter of claim 1, wherein the elongated member comprises plastic.

7. The locking catheter of claim 1, wherein the elongated member comprises a plurality of apertures for allowing fluid into and out of the central lumen of the elongated member.

8. The locking catheter of claim 1, wherein the first proximal member comprises a valve, the valve being open when the first proximal member is coupled to the second proximal member, and the valve being closed when the first proximal member is decoupled from the second proximal member.

9. The locking catheter of claim 1, wherein the first proximal member comprises a ratchet and the second proximal member comprises teeth, the ratchet engaging the teeth when the second proximal member is coupled to the first proximal member and thereby preventing the second proximal member from inadvertently decoupling from the first proximal member.

10. The locking catheter of claim 1, wherein the first proximal member comprises one of a male and female latch and the second proximal member comprises the other of a male and female latch, the male latch comprising a prong, the female latch comprising a notch, the male latch engaging the female latch when the first proximal member is coupled to the second proximal member and thereby preventing the first proximal member from inadvertently decoupling from the second proximal member.

11. The locking catheter of claim 1, wherein the first proximal member comprises a first latch including a first set of teeth and the second proximal member comprises a second latch including a second set of teeth, the first set of teeth engaging the second set of teeth when the first proximal member is coupled to the second proximal member thereby preventing the first proximal member from inadvertently decoupling from the second proximal member.

12. The locking catheter of claim 1, wherein the second proximal member comprises a spool to wind the elongated flexible member therearound when the second proximal member is coupled to the first proximal member.

13. The locking catheter of claim 1, further comprising a second elongated body member defining a central lumen extending therethrough, the elongated body member comprising a first port and a second port, the first port removably couplable to the second proximal member and extending coaxially from the central passageway of the second proximal member, the second port for connecting to a device external to the patient.

14. The locking catheter of claim 13, wherein the first port comprises a valve for sealing the central passageway of the second proximal member when the second port is decoupled from the device external to the patient.

15. The locking catheter of claim 14, wherein the valve comprises a stopcock.

16. A method of locking a catheter in a patient, comprising:

providing a locking catheter comprising:
an elongated body member defining a central lumen and comprising a distal portion and a proximal portion, at least a portion of the elongated body member for placement within a patient,
a first proximal member disposed at the proximal portion of the elongated body member and defining a central passageway extending therethrough and coaxial with the lumen,
an elongated flexible member comprising a first end and a second end, the first end coupled to the distal portion of the elongated body member, the elongated flexible member extending through both at least a portion of the central lumen of the elongated body member and the central passageway of the first proximal member with the second end disposed external to the elongated body member, and
a second proximal member releasably couplable to the first proximal member to allow selective locking and unlocking of the elongated flexible member therebetween, the second proximal member defining a central passageway extending therethrough and a separate channel extending therethrough, the elongated flexible member extending through the separate channel and being slidable therethrough to allow the distal portion of the elongated body member to be drawn toward the proximal portion of the elongated body member;

inserting at least the distal portion of the elongated body member into the patient;

pulling the elongated flexible member through the separate channel of the second proximal member to draw the distal portion of the elongated body member toward the proximal portion of the elongated body member thereby forming a loop in the distal portion; and coupling the first and second proximal members together to compress and lock the elongated flexible member and secure the loop.

17. A locking catheter, comprising:

an elongated body member defining a central lumen and comprising a distal portion and a proximal portion, at least a portion of the elongated body member for placement within a patient;

a first proximal member disposed at the proximal portion of the elongated body member and defining a central passageway extending therethrough and a separate channel extending therethrough, the central passageway being coaxial with the lumen;

an elongated flexible member comprising a first end and a second end, the first end coupled to the distal portion of the elongated body member, the elongated flexible member extending through at least a portion of the central lumen of the elongated body member, the central passageway of the first proximal member, and the separate channel, and being slidable through the separate channel to allow the distal portion of the elongated body member to be drawn toward the proximal portion of the elongated body member to form a loop in the distal portion, with the second end disposed external to the elongated body member; and a second proximal member releasably couplable to the first proximal member to allow selective locking and unlocking of the elongated flexible member therebetween, the second proximal member defining a central passageway extending therethrough, the central passageway of the second proximal member extending coaxially from the central passageway of the first proximal member and the elongated flexible member being compressed between the first and second proximal members and non-slidable through the separate channel to secure the loop when the first and second proximal members are coupled together.

* * * * *